United States Patent
Takimoto et al.

(10) Patent No.: US 8,159,663 B2
(45) Date of Patent: Apr. 17, 2012

(54) LASER MICROSCOPE APPARATUS HAVING A FREQUENCY DISPERSION ADJUSTER

(75) Inventors: Shinichi Takimoto, Tokyo (JP); Takeshi Hashimoto, Saitama (JP); Hirokazu Kubo, Tokyo (JP); Tatsuo Nakata, Tokyo (JP)

(73) Assignee: Olympus Corporation, Tokyo (JP)

( * ) Notice: Subject to any disclaimer, the term of this patent is extended or adjusted under 35 U.S.C. 154(b) by 248 days.

(21) Appl. No.: 12/469,007

(22) Filed: May 20, 2009

(65) Prior Publication Data

US 2009/0290150 A1 Nov. 26, 2009

(30) Foreign Application Priority Data

May 23, 2008 (JP) ................................. 2008-135523

(51) Int. Cl.
*G01J 3/44* (2006.01)
*G01N 21/64* (2006.01)
*G01N 21/65* (2006.01)

(52) U.S. Cl. ........................... 356/301; 356/73; 356/318

(58) Field of Classification Search ................... 356/301
See application file for complete search history.

(56) References Cited

U.S. PATENT DOCUMENTS

| 2003/0007145 A1* | 1/2003 | Shimada ....................... 356/301 |
| 2005/0168735 A1 | 8/2005 | Boppart et al. |
| 2006/0192969 A1 | 8/2006 | Marks et al. |
| 2006/0237666 A1 | 10/2006 | Kubo |
| 2007/0215816 A1 | 9/2007 | Hui et al. |
| 2008/0059135 A1 | 3/2008 | Murugkar et al. |
| 2008/0125977 A1 | 5/2008 | Anquetil et al. |

FOREIGN PATENT DOCUMENTS

| JP | 2002-520612 A | 7/2002 |
| JP | 2002-243641 A | 8/2002 |
| WO | WO 00/04352 A1 | 1/2000 |
| WO | WO 2006/104237 A1 | 10/2006 |
| WO | WO 2008/056702 A1 | 5/2008 |
| WO | WO 2008/127388 A2 | 10/2008 |

OTHER PUBLICATIONS

Extended European Search Report dated Sep. 23, 2009 issued in counterpart European Appln. No. 09006686.1-1234.

* cited by examiner

*Primary Examiner* — F. L. Evans
(74) *Attorney, Agent, or Firm* — Holtz, Holtz, Goodman & Chick, PC (57) ABSTRACT

To enable both observations of coherent anti-Stokes Raman scattering light and multiphoton fluorescence in a same apparatus so as to observe a specimen by various observation methods. There is provided a laser microscope apparatus comprising: two optical paths for guiding pulsed laser beams having two different frequencies whose frequency difference is approximately equal to a specific molecular vibration frequency in a specimen; a multiplexer for combining the pulsed laser beams guided through these two optical paths; and a frequency dispersion adjuster which is provided on at least one of these two optical paths, and is capable of adjustment to approximately equalize frequency dispersion quantities of the pulsed laser beams guided through the two optical paths.

17 Claims, 4 Drawing Sheets

FIG. 4B

LASER MICROSCOPE APPARATUS HAVING A FREQUENCY DISPERSION ADJUSTER

BACKGROUND OF THE INVENTION

1. Field of the Invention

The present invention relates to a laser microscope apparatus.

This application is based on Japanese Patent Application No. 2008-135523, the content of which is incorporated herein by reference.

2. Description of Related Art

There is a known coherent anti-Stokes Raman scattering microscope with which a specimen is observed through generation and detection of coherent anti-Stokes Raman scattering light from a molecule in the specimen utilizing its specific molecular vibration (for example, refer to Japanese Unexamined Patent Application, Publication No. 2002-520612). Since this coherent anti-Stokes Raman scattering microscope utilizes a specific molecular vibration in the specimen, there is no need to previously label the observation target with a fluorescence probe likewise of a fluorescence microscope. In addition, the molecule for observation can be changed by changing the vibration to use.

Conventionally, for the light source of such a coherent anti-Stokes Raman scattering microscope, a picosecond pulsed laser having two different frequencies of relatively narrow frequency spectral bands has been used. In a state where the frequency difference between these two picosecond pulsed laser beams is adjusted to correspond to the specific molecular vibration frequency in the specimen, light is focused on the specimen surface. At this time, in an extremely narrow space of a high photon density spreading in the vicinity of the focal plane, the frequency difference between these two picosecond pulsed laser beams resonates with the specific molecular vibration frequency to thereby generate strong coherent anti-Stokes Raman scattering light. This coherent anti-Stokes Raman scattering light has a higher frequency (that is to say, a shorter wavelength) than the frequencies of the irradiated two picosecond pulsed laser beams. Accordingly, the molecule in the specimen can be observed by spectrally selecting and detecting this coherent anti-Stokes Raman scattering light alone.

In addition, there is also known a multiphoton excitation type laser microscope in which femtosecond pulsed laser beams are focused on the specimen surface to thereby increase the photon density in an extremely narrow space spreading in the vicinity of the focal plane so as to cause multiphoton excitation of a fluorophore so that a sharp fluorescence image can be obtained (for example, refer to Japanese Unexamined Patent Application, Publication No. 2002-243641).

However, in order to efficiently generate coherent anti-Stokes Raman scattering light from a specific molecular vibration in the specimen using such a coherent anti-Stokes Raman scattering microscope, picosecond pulsed laser beams of narrow frequency bands (or, relatively broad pulse widths) need to be used. This is because that, when pulsed laser beams of broad frequency spectral bands are used, the frequency difference between these two pulsed laser beams may contain frequency difference components not corresponding to the specific molecular vibration frequency. These frequency difference components not corresponding to the specific molecular vibration frequency do not resonate with the specific molecular vibration frequency, and thus do not contribute to the generation of coherent anti-Stokes Raman scattering light. As a result, energies of two pulsed laser beams can not be efficiently utilized for the generation of coherent anti-Stokes Raman scattering light from the specific molecular vibration.

On the other hand, in the multiphoton excitation type laser microscope, for the purpose of increasing fluorescence excitation efficiency and of reducing the damage on the specimen to carry out the observation, femtosecond laser beams of broad frequency spectral bands (or, extremely narrow pulse widths) are used; in addition of which, these beams are in a state close to the Fourier-limited pulse. From the above reasons, the both observation methods with the coherent anti-Stokes Raman scattering microscope and the multiphoton excitation type laser microscope are different in the spec of pulsed laser beams to be used, and thus are difficult to achieve in a same microscope apparatus.

BRIEF SUMMARY OF THE INVENTION

The present invention provides a laser microscope apparatus capable of both observations of coherent anti-Stokes Raman scattering light and multiphoton fluorescence in a same apparatus, and capable of observing a specimen by various observation methods.

The present invention provides a laser microscope apparatus comprising: two optical paths for guiding pulsed laser beams having two different frequencies whose frequency difference is approximately equal to a specific molecular vibration frequency in a specimen; a multiplexer for combining the pulsed laser beams guided through these two optical paths; and a frequency dispersion adjuster which is provided on at least one of these two optical paths, and is capable of adjustment to approximately equalize frequency dispersion quantities of the pulsed laser beams guided through the two optical paths.

Each guided pulsed laser beam can be given an equal frequency dispersion quantity by the frequency dispersion adjuster. By having a frequency dispersion, frequency components of the frequency spectrum of each pulsed laser beam can be distributed on the time axis. For this reason, even a pulsed laser beam having a relatively broad frequency spectral band such as a femtosecond laser beam can be regarded to have a relatively narrow frequency spectral band at each time point on the time axis, by adjusting the frequency dispersion quantity. In addition, the frequency difference between these two pulsed laser beams can be always kept constant at each time point on the time axis, by adjusting the frequency dispersion quantity of each guided pulsed laser beam.

In this manner, by focusing two pulsed laser beams in a state where their frequency difference is kept constant on the time axis, coherent anti-Stokes Raman scattering light is generated from the vibration of a molecule whose frequency is equal to the frequency difference between these two pulsed laser beams, among other molecules in the specimen. At this time, since the frequency difference between the two pulsed laser beams is kept constant on the time axis, energies of these two pulsed laser beams can be efficiently utilized for the generation of coherent anti-Stokes Raman scattering light.

As described above, even if pulsed laser beams of relatively broad frequency bands such as femtosecond laser beams are used, coherent anti-Stokes Raman scattering light can be efficiently generated. On the other hand, use of such pulsed laser beams having relatively broad frequency bands such as femtosecond laser beams enables a multiphoton excitation effect to occur by focusing either one pulsed laser beam of two pulsed laser beams on the specimen. That is to say, the present invention is capable of both observations of coherent anti-Stokes Raman scattering light and of multiphoton fluorescence with one laser microscope apparatus.

In the laser microscope apparatus according to this invention, further, the structure of the frequency dispersion adjuster is desirably capable of adjustment of a frequency dispersion quantity so that a pulsed laser beam on a surface of the specimen can be closer to its approximate Fourier-limited pulse. According to this structure, the approximate Fourier-limited pulse can be achieved on the surface of the specimen by adjusting the dispersion quantity of a pulsed laser beam using the frequency dispersion adjuster. By so doing, multiphoton fluorescence can be more efficiently generated in the multiphoton fluorescence observation so that sharp multiphoton fluorescence images can be observed.

In the laser microscope apparatus according to this invention, the structure may also comprise: a laser light source which emits a femtosecond pulsed laser beam; a branching section which splits the femtosecond pulsed laser beam emitted from the laser light source into the two optical paths; and a frequency converter which is provided on either one of these optical paths, and gives a frequency difference approximately equivalent to the specific molecular vibration frequency in the specimen, to femtosecond pulsed laser beams guided through the two optical paths.

According to this structure, pulsed laser beams having two different frequencies can be obtained by splitting a femtosecond pulsed laser beam emitted from the single laser light source, and converting the frequency of the femtosecond pulsed laser beam on either one of these optical paths with the frequency converter so that a frequency difference approximately equal to the specific molecular vibration frequency in the specimen is given. By so doing, one single laser light source can be commonly used for two pulsed laser beams having different frequencies to simplify the apparatus structure.

In the laser microscope apparatus according to this invention, the structure may also comprise a pulse timing adjuster which is provided on either one of these two optical paths, and is capable of adjustment of a timewise timing between the pulsed laser beams guided through the two optical paths, on a surface of the specimen. By adjusting the timewise timing of one pulsed laser beam with respect to the other pulsed laser beam, the frequency difference between the two pulsed laser beams can be arbitrarily adjusted within the frequency bands of these two pulsed laser beams.

By so doing, by adjusting the timing between two pulsed laser beams on the surface of the specimen, the timings of two pulsed laser beams can be adjusted to correspond to the specific molecular vibration frequency in the specimen. By so doing, coherent anti-Stokes Raman scattering light can be efficiently generated. In addition, since the frequency difference can be arbitrarily adjusted, the frequency difference can also correspond to the vibration frequency of another molecule in the specimen.

In the laser microscope apparatus according to this invention, the frequency converter may also be a photonic crystal fiber. By using a photonic crystal fiber as the frequency converter, pulsed laser beams having broad frequency spectral bands with a given frequency dispersion can be readily obtained at low price. In addition, by selecting the type of the photonic crystal fiber to use, pulsed laser beams having various frequency spectral components and bands can be obtained. For this reason, the frequency difference between two pulsed laser beams can be adjusted to correspond to various vibration frequencies of molecules in the specimen.

In the laser microscope apparatus according to this invention, the structure may also comprise a light intensity adjuster which adjusts a light intensity of the pulsed laser beam. According to this structure, the light intensity adjuster can be operated to adjust the light intensity of a pulsed laser beam on each optical path so that the light intensity can be balanced for the generation of coherent anti-Stokes Raman scattering light and/or multiphoton fluorescence, and optimum images can be observed.

The present invention demonstrates an effect in which both observations of coherent anti-Stokes Raman scattering light and multiphoton fluorescence can be performed in a same apparatus, and a specimen can be observed by various observation methods.

DETAILED DESCRIPTION OF THE INVENTION

Hereunder is a description of a laser microscope apparatus 1 according to one embodiment of the present invention, with reference to FIG. 1 to FIG. 4.

Figure 1:
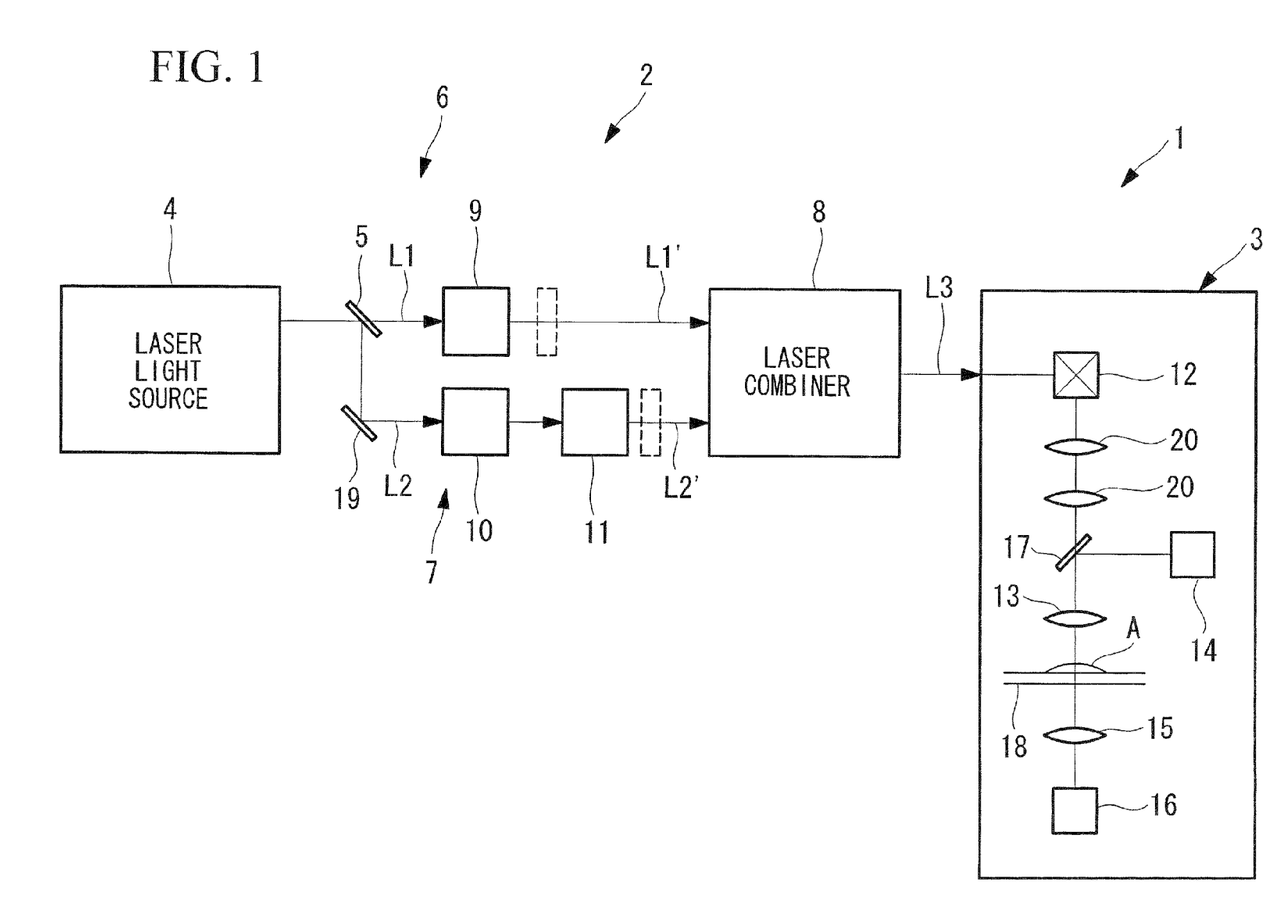
FIG. 1 is a block diagram showing the overall structure of a laser microscope apparatus according to one embodiment of the present invention.

As shown in FIG. 1, the laser microscope apparatus 1 according to this embodiment comprises a laser light source device 2, and a microscope mainbody 3 for observing a specimen A by irradiation of laser beams from the laser light source device 2 onto the specimen A.

The laser light source device 2 comprises a single laser light source 4 which emits a femtosecond pulsed laser beam, a beam splitter (branching section) 5 which splits the femtosecond pulsed laser beam emitted from the laser light source 4 into two beams, two optical paths 6 and 7 through which the two femtosecond pulsed laser beams L1 and L2 that have been split by the beam splitter 5 are respectively transmitted, and a laser combiner 8 which combines two pulsed laser beams L1' and L2' that have been transmitted through these two optical paths 6 and 7.

On the first optical path 6 is provided a frequency dispersion device (frequency dispersion adjuster) 9 which is capable of adjustment of a frequency dispersion quantity to give to the femtosecond pulsed laser beam L1. On the second optical path 7 are provided a photonic crystal fiber (frequency converter) 10 through which the femtosecond pulsed laser beam L2 is transmitted, and an optical path adjuster (pulse timing adjuster) 11 which adjusts the length of the optical path of the pulsed laser beam L2' after passing through the photonic crystal fiber 10.

The frequency dispersion device 9 comprises, for example, a pair of prisms (not shown) the gap between which is controllable, and a mirror (not shown). The configuration is such that the femtosecond pulsed laser beam L1 transmitted through the pair of prisms is returned by the mirror, and then is retransmitted through the pair of prisms to go back to the same optical path 6. In this case, the frequency dispersion quantity to give to the pulsed laser beam L1' passing through the frequency dispersion device 9 can be adjusted by controlling the gap between the prisms. In addition, a diffraction grating (not shown) may also be used instead of such prisms.

The frequency dispersion device 9 may also be, for example, a member (not shown) composed of a material having predetermined frequency dispersion properties such as a wedge-shaped glass plate of a changeable thickness. Because of the primitive frequency dispersion properties of the member, a predetermined frequency dispersion can be given to the femtosecond pulsed laser beam L1 passing through the member. The frequency dispersion quantity give can be adjusted by controlling the thickness of the member in a position through which the femtosecond pulsed laser beam L1 passes. In addition, the frequency dispersion device 9 may also be an optical fiber which has been prepared to give a desired dispersion quantity.

In this embodiment, the frequency dispersion device 9 is designed to be capable of setting the dispersion quantity so that the pulsed laser beam L1' passing through the frequency dispersion device 9 can be closer to its approximate Fourier-limited pulse on the surface of the specimen A. By so doing, the expanse of the pulse width of the femtosecond pulsed laser beam L1 can be compensated by the frequency dispersion generated all over the optical path from the laser light source 4 to the specimen A, so that the femtosecond pulsed laser beam at the time when focused on the specimen A can achieve a pulse width close to the approximate Fourier-limit.

The photonic crystal fiber 10 can alter or broaden the frequency band of the femtosecond pulsed laser beam L2 to be transmitted therethrough. The pulsed laser beam L2' transmitted through the photonic crystal fiber 10 is given a frequency dispersion in accordance with the type of the photonic crystal fiber and the condition of the femtosecond pulsed laser beam to transmit. As to the frequency converter, instead of the photonic crystal fiber 10, there may also be employed, for example, any one of a bulk, a thin film, a film, and a photonic crystal structure having similar functions and effects.

The pulse timing adjuster 11 comprises, for example, mirrors (reflectors) (not shown). The length of the optical path of the pulsed laser beam L2' can be changed by folding the optical path of the pulsed laser beam L2' using at least two sets of reflectors, and by controlling gaps between at least two sets of these reflectors. By so doing, the timewise pulse timing of the pulsed laser beam L2' can be adjusted.

In this embodiment, the timewise pulse timing between the pulsed laser beams L1' and L2' which have been transmitted through the two optical paths 6 and 7 and are incident into the laser combiner 8, can be adjusted by the pulse timing adjuster 11 so that the frequency difference $\Omega'$ between the two pulsed laser beams L1' and L2' can correspond to the specific vibration frequency $\Omega$ of a molecule in the specimen A, on the surface of the specimen A. By so doing, coherent anti-Stokes Raman scattering light can be efficiently generated. In addition, the frequency difference $\Omega'$ can be arbitrarily adjusted, and thus can correspond to the vibration frequency of another molecule in the specimen A.

The microscope mainbody 3 is, for example, a laser scanning type microscope comprising a scanner 12 for two-dimensionally scanning a pulsed laser beam L3 emitted from the laser light source device 2, a group of lenses 20, an objective lens 13 which condenses the pulsed laser beam L3 that has been scanned by the scanner 12 on the surface of the specimen A, a first photodetector 14 which detects fluorescence generated from the specimen A and condensed by the objective lens 13, an objective lens 15 which condenses coherent anti-Stokes Raman scattering light generated in a direction penetrating the specimen A, and a second photodetector 16 which detects the coherent anti-Stokes Raman scattering light condensed by the objective lens 15.

In FIG. 1, the reference sign 17 denotes a dichroic mirror, the reference sign 18 denotes a stage, and the reference sign 19 denotes a mirror. The fluorescence generated from the specimen A may also be condensed by the objective lens 15 and detected by the second detector 16. The coherent anti-Stokes Raman scattering light generated from the specimen A may also be condensed by the objective lens 13 and detected by the first detector 14.

Hereunder is a description of the operation of the thus configured laser microscope apparatus 1 according to this embodiment.

In order to observe the specimen A with coherent anti-Stokes Raman scattering light using the laser microscope apparatus 1 of this embodiment, the laser light source 4 is operated to emit a femtosecond pulsed laser beam. The femtosecond pulsed laser beam emitted from the laser light source 4 is split into two optical paths 6 and 7 by the beam splitter 5.

The femtosecond pulsed laser beam L1 split into the first optical path 6 is transmitted through the frequency dispersion device 9 arranged on the first optical path 6, by which an initial frequency dispersion quantity is given. On the other hand, the femtosecond pulsed laser beam L2 split into the second optical path 7 is deflected by the mirror 19, and then is transmitted through the photonic crystal fiber 10, by which the frequency spectrum thereof is altered or broadened so that the beam has a broader band (pulsed laser beam L2') as compared to the femtosecond pulsed laser beam L1 on the first optical path 6. At the same time, the pulsed laser beam L2' is given a predetermined frequency dispersion by the photonic crystal fiber 10.

Figure 2A:
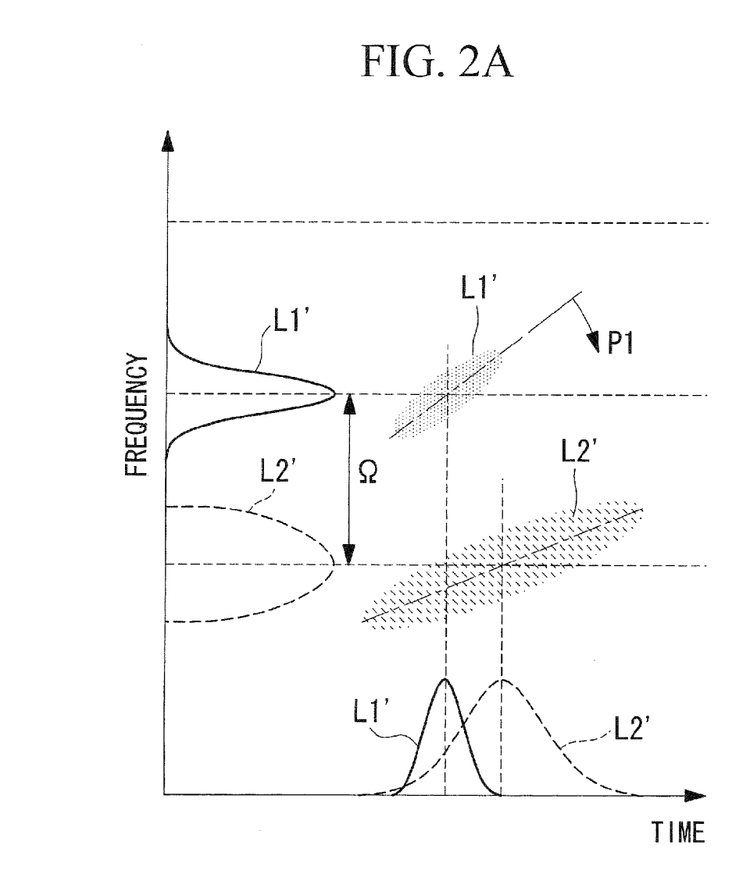
FIG. 2A is a graph showing the time distributions of frequencies of pulsed laser beams transmitted through two optical paths of the laser microscope apparatus of FIG. 1, before adjustment of the frequency dispersion quantity.

If the initial frequency dispersion quantity given to the pulsed laser beam L1' by the frequency dispersion device 9 and the frequency dispersion quantity given to the pulsed laser beam L2' by passing through the photonic crystal fiber 10 are different, as shown in FIG. 2A, inclinations of the frequency distributions of the pulsed laser beams L1' and L2' differ on the time axis. In this case, the frequency difference $\Omega'$ between the pulsed laser beams L1' and L2' transmitted through the two optical paths 6 and 7 varies at each time on the time axis, and is not kept constant. In this state, energies of these pulsed laser beams L1' and L2' can not be efficiently utilized for the generation of coherent anti-Stokes Raman scattering light from the specific molecular vibration in the specimen A.

Therefore, in this embodiment, the frequency dispersion device 9 is operated to adjust the dispersion quantity given to the pulsed laser beam L1' passing through the first optical path 6 to be approximately equal to the dispersion quantity given to the pulsed laser beam L2' passing through the photonic crystal fiber 10 on the second optical path 7 on the surface of the specimen A. That is to say, as shown by the arrow P1 of FIG. 2A, the inclination of the frequency distribution in the time axis direction is changed.

Figure 2B:
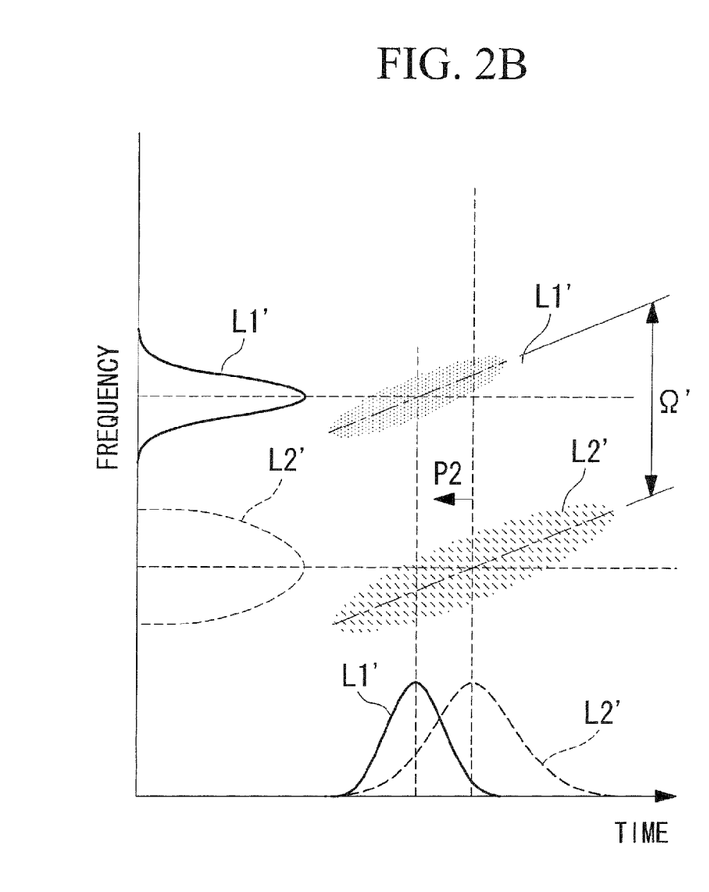
FIG. 2B is a graph showing the time distributions of frequencies of pulsed laser beams transmitted through two optical paths of the laser microscope apparatus of FIG. 1, after adjustment of the frequency dispersion quantity.

Even in a state where the frequency difference Ω' between the two pulsed laser beams L1' and L2' is kept constant on the time axis, as shown in FIG. 2B, the frequency difference Ω' between the two pulsed laser beams L1' and L2' may not correspond to the specific molecular vibration frequency Ω' in the specimen A, depending on the timewise pulse timing between the pulsed laser beams L1' and L2'. Therefore, in this embodiment, the pulse timing adjuster 11 is operated to delay the pulsed laser beam L2' passing through the second optical path 7 in the time axis direction. That is to say, as shown by the arrow P2 of FIG. 2B, the timewise pulse timing of the pulsed laser beam L2' is adjusted.

Figure 3:
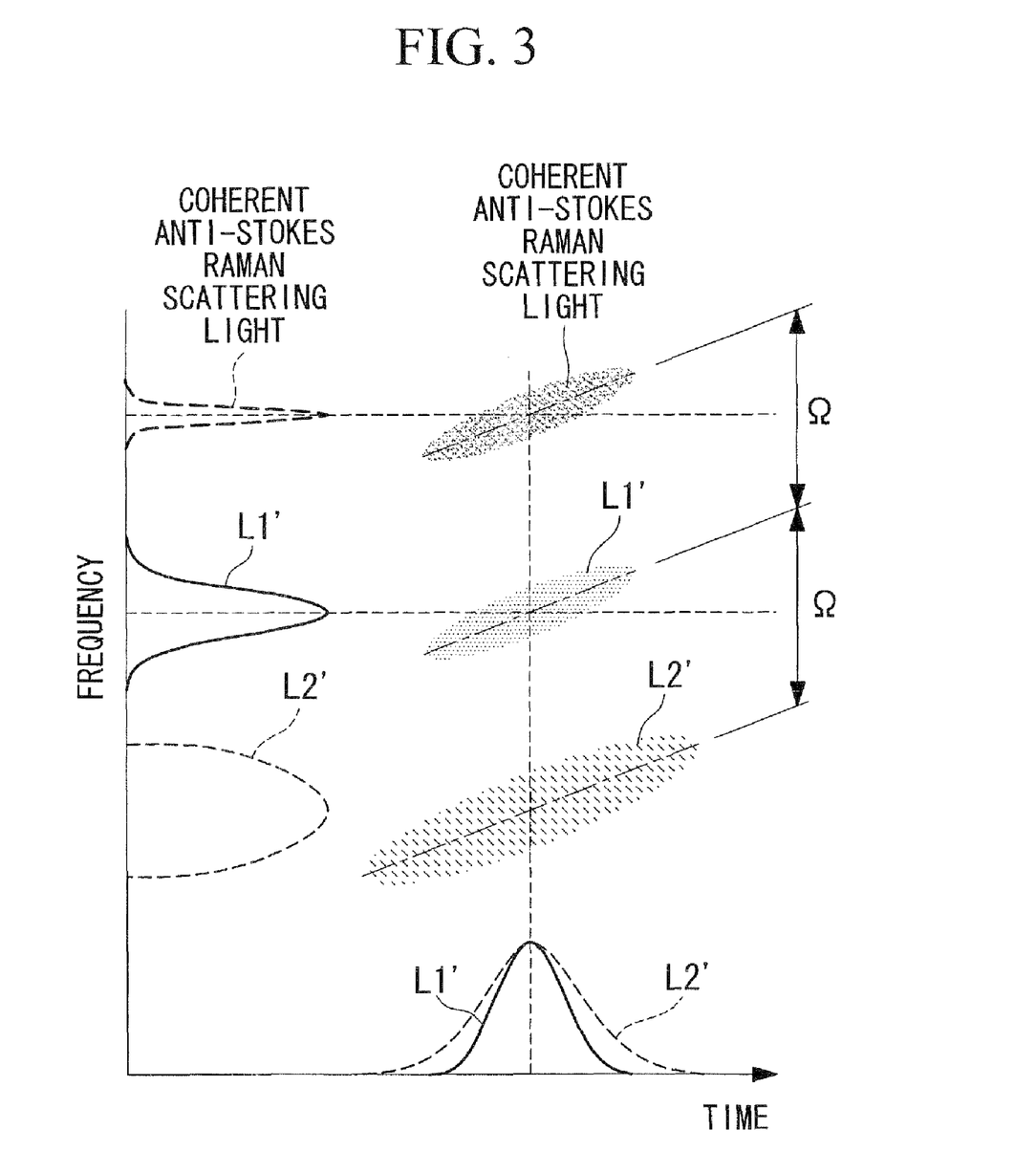
FIG. 3 is a graph showing the time distributions of frequencies of pulsed laser beams transmitted through two optical paths of the laser microscope apparatus of FIG. 1, after adjustment of the timewise pulse timing.

By so doing, as shown in FIG. 3, the frequency dispersion quantity and the frequency difference Ω' between the pulsed laser beams L1' and L2' on the two optical paths 6 and 7 leading to the laser combiner 8 are adjusted. Then, the pulsed laser beams L1' and L2' are combined by the laser combiner 8 to become the pulsed laser beam L3. In addition, the frequency difference Ω' between the pulsed laser beams L1' and L2' can be arbitrarily adjusted. For this reason, the timewise pulse timing between the two pulsed laser beams L1' and L2' can be adjusted on the surface of the specimen A so that the timewise pulse timings of the two pulsed laser beams can correspond to the specific molecular vibration frequency Ω in the specimen A.

The thus composed pulsed laser beam L3 is made incident into the microscope mainbody 3, then two-dimensionally scanned by the scanner 12, and focused on the surface of the specimen A through the lens group 20 and the objective lens 13. By so doing, in each position where the pulsed laser beam L3 is focused, coherent anti-Stokes Raman scattering light can be generated from the specific molecular vibration frequency Ω in the specimen A.

In cases where the frequency dispersion quantities or the timewise pulse timings of the pulsed laser beams L1' and L2' are changed by the optical system after the laser combiner 8, the frequency dispersion quantity and the timewise pulse timing may be readjusted so that the frequency difference Ω' between the pulsed laser beams L1' and L2' can correspond to the specific molecular vibration frequency Ω in the specimen A, on the surface of the specimen A.

The coherent anti-Stokes Raman scattering light generated from the specimen A is focused by the objective lens 15 arranged on the opposite side of the objective lens 13 across the specimen A, and is detected by the second photodetector 16. Then, the coordinate of the position where the pulsed laser beam L3 is focused on the surface of the specimen A and the intensity of the coherent anti-Stokes Raman scattering light detected by the second photodetector 16 are linked and stored, by which a two-dimensional image of coherent anti-Stokes Raman scattering light can be obtained. The coherent anti-Stokes Raman scattering light generated from the specimen A may also be focused by the objective lens 13, branched by the dichroic mirror 17, and detected by the first photodetector 14.

In this case, according to this embodiment, since the frequency difference Ω' between the pulsed laser beams L1' and L2' on the two optical paths 6 and 7 corresponds to the specific molecular vibration frequency Ω in the specimen A at each time on the time axis, energies of the pulsed laser beams L1' and L2' can be efficiently utilized for the generation of coherent anti-Stokes Raman scattering light from the specific molecular vibration frequency Ω in the specimen A. Time integration of the thus generated coherent anti-Stokes Raman scattering light can yield a bright image of coherent anti-Stokes Raman scattering light.

Figure 4A:
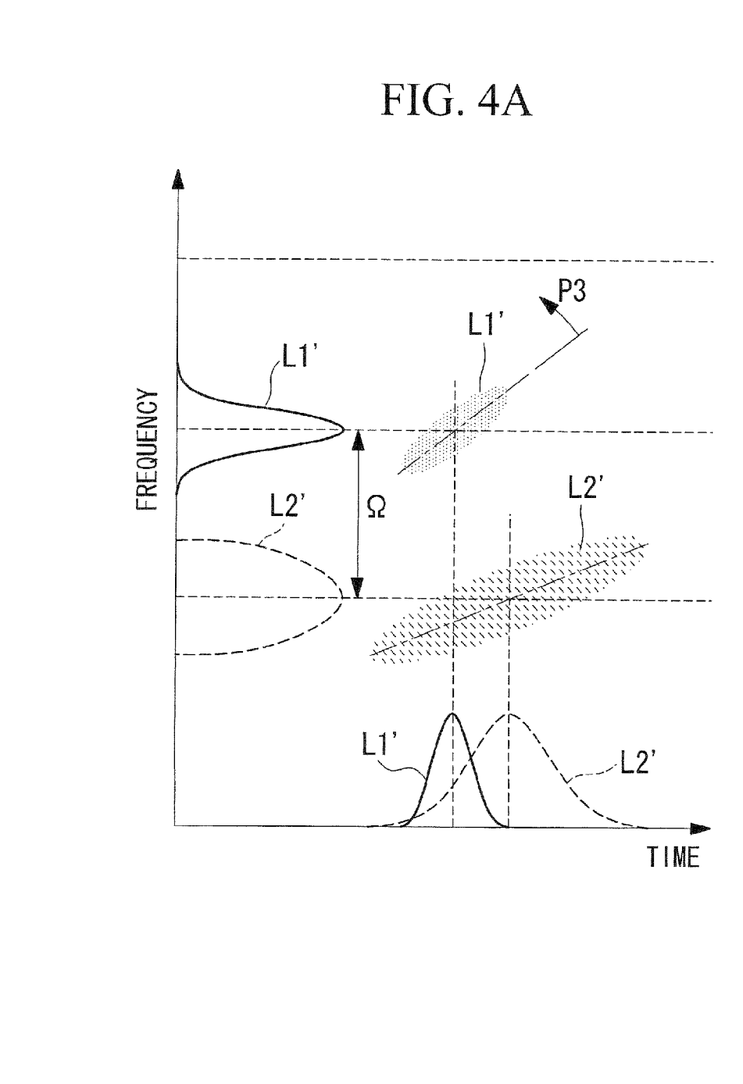
FIG. 4A is a graph showing the time distributions of frequencies of pulsed laser beams transmitted through two optical paths of the laser microscope apparatus of FIG. 1, in a state before adjustment of the frequency dispersion quantity between these pulsed laser beams in the observation of multiphoton excitation fluorescence.
Figure 4B:
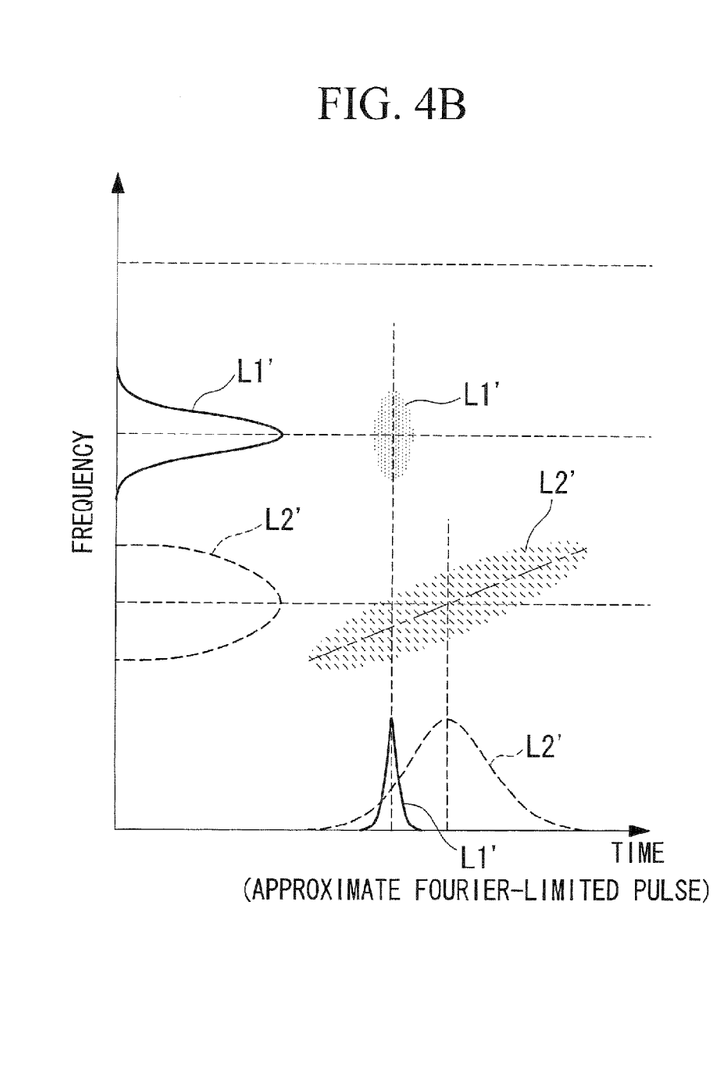
FIG. 4B is a graph showing the time distributions of frequencies of pulsed laser beams transmitted through two optical paths of the laser microscope apparatus of FIG. 1, in a state after adjustment of the frequency dispersion quantity between these pulsed laser beams in the observation of multiphoton excitation fluorescence.

In this embodiment, by operating the frequency dispersion device 9, the frequency dispersion quantity to give to the pulsed laser beam L1' passing through the first optical path 6 can be adjusted as shown by the arrow P3 of FIG. 4A, and the frequency dispersion quantity of the pulsed laser beam L1' can be set so that the pulsed laser beam L1' can be closer to its approximate Fourier-limited pulse on the surface of the specimen A as shown in FIG. 4B. As a result, through focusing the thus set pulsed laser beam L1' on the specimen A with the objective lens 13, fluorescence by multiphoton excitation can be efficiently generated in the position of focused light on the specimen A.

The fluorescence generated from the specimen A is focused by the objective lens 13, then is branched by the dichroic mirror 17, and is detected by the first photodetector 14. Then, the coordinate of the position where the pulsed laser beam L1' is focused on the surface of the specimen A and the fluorescence intensity detected by the first photodetector 14 are linked and stored, by which a two-dimensional image of multiphoton fluorescence can be obtained. The fluorescence generated from the specimen A may also be focused by the objective lens 15, and detected by the second photodetector 16.

Moreover, SHG light (second harmonic generation light) can also be observed under the same condition as that of the observation for multiple excitation fluorescence.

In this way, according to the laser microscope apparatus 1 of this embodiment, observation of coherent anti-Stokes Raman scattering light, observation of multiphoton excitation fluorescence, and observation of SHG light can be efficiently performed while switching over therebetween. That is to say, with one laser microscope apparatus 1, three types of observations can be efficiently performed to achieve multimodal observation.

If the excitation efficiency of multiphoton excitation fluorescence or SHG light do not matter to some extent, the above three types of observations can be simultaneously performed without switching over. The first and second photodetectors 14 and 16 may also be allocated as a detector for detecting any one of coherent anti-Stokes Raman scattering light, multiphoton excitation fluorescence, and SHG light. If the number of photodetectors is insufficient, another photodetector may be newly added in a position equivalent to either one of the first and second photodetectors 14 and 16.

In this case, it is sufficient to prepare a laser light source which emits a femtosecond pulsed laser beam as the laser light source 4, and there is no need to newly prepare a laser light source which emits a picosecond pulsed laser beam for the generation of coherent anti-Stokes Raman scattering light. Therefore, the apparatus can be made simple at low price.

Moreover, since the photonic crystal fiber 10 is used as the frequency converter, the apparatus can be made much simpler at lower price. In addition, since the pulse timing adjuster 11 is constituted by mirrors (reflectors), the apparatus can be made even simpler at lower price.

According to the laser microscope apparatus 1 of this embodiment, the timewise pulse timing between the pulsed laser beams L1' and L2' passing through the two optical paths 6 and 7 can be adjusted by the pulse timing adjuster 11 so that the frequency difference Ω' can be freely adjusted within respective frequency spectral bands of the pulsed laser beams L1' and L2'. Therefore, the frequency difference Ω' between the pulsed laser beams L1' and L2' may approximately correspond to the specific molecular vibration frequency Ω' in the specimen A to some extent, and does not have to be strictly accurate.

That is to say, there is no need to accurately alter or broaden the frequency spectral band of the femtosecond pulsed laser beam L2 by passing through the photonic crystal fiber 10. The pulse timing adjuster 11 can achieve the accurate correspondence to the specific molecular vibration frequency Ω in the specimen A, so that coherent anti-Stokes Raman scattering light can be most efficiently generated from the specific molecular vibration frequency Ω in the specimen A, by which a bright image of the coherent anti-Stokes Raman scattering light can be obtained.

In this embodiment, there have been employed the single laser light source 4 which emits a femtosecond pulsed laser beam and the beam splitter 5 which splits such a beam into the optical paths 6 and 7; however, instead of them, a plurality of light sources 4 may be furnished for respective optical paths 6 and 7 on a one-to-one basis. In this case, the respective laser light sources 4 have to be synchronous with each other in terms of the pulse timing.

As to the frequency dispersion device 9, there has been exemplified a device which comprises a pair of prisms and a mirror to be capable of continuously changing the frequency dispersion quantity; however, instead of this, there may also be employed a system in which a plurality of devices of fixed frequency dispersion quantities are provided to be switched over in a stepwise manner, or a system which is detachable onto the first optical path 6 to switch over the dispersion quantity to give to the pulsed laser beam L1'.

The frequency dispersion device 9 may be provided on the second optical path 7, and may also be respectively provided on both of the optical paths 6 and 7.

A light intensity adjuster (dotted line regions in FIG. 1) such as a neutral density filter may also be arranged on at least either one of the optical paths 6 and 7. By so doing, the light intensity can be balanced between the pulsed laser beams L1' and L2' passing through the two optical paths 6 and 7. Particularly, besides a neutral density filter, a combination of a polarization beam splitter and a rotatable half-wave plate, an acoustooptic device, an electro-optic element, or the like may also be used as a light intensity adjuster.

For the observation of multiphoton excitation fluorescence performed by setting the frequency dispersion quantity to give to the pulsed laser beam L1' passing through the first optical path 6 so as to be closer to its approximate Fourier-limited pulse on the surface of the specimen A, the second optical path 7 may be limited by a shutter or the like. Since it becomes unnecessary to split into the second optical path 7 for the observation of multiphoton excitation fluorescence, the limitation thereof can enable to reduce the noise occurring in the multiphoton fluorescence image and the damage onto the specimen A.

What is claimed is:

1. A laser microscope apparatus comprising:
   two optical paths for guiding pulsed laser beams having two different frequencies whose frequency difference is approximately equal to a specific molecular vibration frequency in a specimen;
   a multiplexer for combining the pulsed laser beams guided through the two optical paths; and
   a frequency dispersion adjuster which is provided on at least one of the two optical paths, and is capable of keeping the frequency difference between the two pulsed laser beams constant at each time point on a time axis by adjusting a frequency dispersion quantity of the at least one of the pulsed laser beams that is guided through the at least one of the two optical paths.

2. A laser microscope apparatus according to claim 1, wherein the frequency dispersion adjuster is capable of performing adjustment of a frequency dispersion quantity so that a pulsed laser beam on a surface of the specimen is closer to its approximate Fourier-limited pulse.

3. A laser microscope apparatus according to claim 1, further comprising:
   a laser light source which emits a femtosecond pulsed laser beam;
   a branching section which splits the femtosecond pulsed laser beam emitted from the laser light source into the two optical paths; and
   a frequency converter which is provided on one of the two optical paths, and gives a frequency difference approximately equivalent to the specific molecular vibration frequency in the specimen, to femtosecond pulsed laser beams guided through the two optical paths.

4. A laser microscope apparatus according to claim 1, further comprising a pulse timing adjuster which is provided on one of the two optical paths, and is capable of performing adjustment of a timewise timing between the pulsed laser beams guided through the two optical paths, on a surface of the specimen.

5. A laser microscope apparatus according to claim 3, wherein the frequency converter is a photonic crystal fiber.

6. A laser microscope apparatus according to claim 1, further comprising a light intensity adjuster which is provided on at least one of the two optical paths, and adjusts a light intensity of the at least one of the pulsed laser beams that is guided through the at least one of the two optical paths.

7. A laser microscope apparatus comprising:
   two optical paths for guiding pulsed laser beams having two different frequencies whose frequency difference is approximately equal to a specific molecular vibration frequency in a specimen;
   a multiplexer for combining the pulsed laser beams guided through the two optical paths;
   a frequency dispersion adjuster which is provided on at least one of the two optical paths, and is capable of performing adjustment to approximately equalize frequency dispersion quantities of the pulsed laser beams guided through the two optical paths;
   a laser light source which emits a femtosecond pulsed laser beam;
   a branching section which splits the femtosecond pulsed laser beam emitted from the laser light source into the two optical paths; and
   a frequency converter which is provided on one of the two optical paths, and gives a frequency difference substantially equivalent to the specific molecular vibration frequency in the specimen, to femtosecond pulsed laser beams guided through the two optical paths.

8. A laser microscope apparatus according to claim 7, wherein the frequency dispersion adjuster is capable of performing adjustment of frequency dispersion quantity so that a pulsed laser beam on a surface of the specimen is closer to its approximate Fourier-limited pulse.

9. A laser microscope apparatus according to claim 7, further comprising a pulse timing adjuster which is provided on one of the two optical paths, and is capable of performing adjustment of a timewise timing between the pulsed laser beams guided through the two optical paths, on a surface of the specimen.

10. A laser microscope apparatus according to claim 7, wherein the frequency converter is a photonic crystal fiber.

11. A laser microscope apparatus according to claim 7, further comprising a light intensity adjuster which is provided on at least one of the two optical paths, and adjusts a light intensity of the at least one of the pulsed laser beams that is guided through the at least one of the two optical paths.

12. A laser microscope apparatus comprising:
two optical paths for guiding pulsed laser beams having two different frequencies whose frequency difference is approximately equal to a specific molecular vibration frequency in a specimen;
a multiplexer for combining the pulsed laser beams guided through the two optical paths;
a frequency dispersion adjuster which is provided on at least one of the two optical paths, and is capable of performing adjustment to approximately equalize frequency dispersion quantities of the pulsed laser beams guided through the two optical paths; and
a light intensity adjuster which is provided on at least one of the two optical paths, and which adjusts a light intensity of the at least one of the pulsed laser beams that is guided through the at least one of the two optical paths.

13. A laser microscope apparatus according to claim 12, wherein the frequency dispersion adjuster is capable of performing adjustment of a frequency dispersion quantity so that a pulsed laser beam on a surface of the specimen is closer to its approximate Fourier-limited pulse.

14. A laser microscope apparatus according to claim 12, further comprising a pulse timing adjuster which is provided on one of the two optical paths, and is capable of performing adjustment of a timewise timing between the pulsed laser beams guided through the two optical paths, on a surface of the specimen.

15. An observing method of a coherent anti-Stokes Raman scattering light, the method comprising:
generating two pulsed laser beams each having a different frequency;
adjusting a frequency dispersion quantity of at least one of the two laser pulsed beams so that a specimen is irradiated with the two pulsed laser beams in a state in which a frequency difference between the two pulsed laser beams is kept constant at each time point on a time axis, by substantially matching the frequency dispersion quantities of the two pulsed laser beams;
irradiating the specimen with the adjusted laser beams; and
detecting the coherent anti-Stokes Raman scattering light obtained based on the frequency difference.

16. The observing method according to claim 15, wherein the frequency difference between the two pulsed laser beams is adjusted so as to be substantially equal to a predetermined vibration frequency of a molecule in the specimen.

17. The observing method according to claim 16, wherein the adjustment of the frequency difference is performed by adjusting a pulse timing between the two pulsed laser beams.

* * * * *